(12) United States Patent
Bosch (10) Patent No.: US 11,124,768 B2
(45) Date of Patent: Sep. 21, 2021

(54) OPTIMALLY ACTIVATED DENDRITIC CELLS THAT INDUCE AN IMPROVED OR INCREASED ANTI-TUMOR IMMUNE RESPONSE

(71) Applicant: Northwest Biotherapeutics, Inc., Bethesda, MD (US)

(72) Inventor: Marnix Leo Bosch, Clyde Hill, WA (US)

(73) Assignee: Northwest Biotherapeutics, Inc., Bethesda, MD (US)

( * ) Notice: Subject to any disclaimer, the term of this patent is extended or adjusted under 35 U.S.C. 154(b) by 0 days.

(21) Appl. No.: 15/740,094

(22) PCT Filed: Jun. 29, 2016

(86) PCT No.: PCT/US2016/040134
§ 371 (c)(1),
(2) Date: Dec. 27, 2017

(87) PCT Pub. No.: WO2017/004230
PCT Pub. Date: Jan. 5, 2017

(65) Prior Publication Data
US 2018/0187145 A1    Jul. 5, 2018

Related U.S. Application Data

(60) Provisional application No. 62/187,086, filed on Jun. 30, 2015.

(51) Int. Cl.
*C12N 5/0784*    (2010.01)
*A61K 35/15*    (2015.01)
(Continued)

(52) U.S. Cl.
CPC .............. *C12N 5/064* (2013.01); *A61K 35/15* (2013.01); *A61K 39/0011* (2013.01);
(Continued)

(58) Field of Classification Search
CPC ................ A61K 39/0011; A61K 35/15; A61K 2039/5154; C12N 5/064; C12N 2506/11; C12N 2501/22; A61P 35/00
See application file for complete search history.

(56) References Cited

U.S. PATENT DOCUMENTS 9,102,917 B2 *  8/2015  Tjoa ..................... C12N 5/0639
2004/0203143 A1  10/2004  Tjoa et al.
(Continued)

FOREIGN PATENT DOCUMENTS

JP    2002-536013 A5    10/2002
JP      201507133 A      6/2015
(Continued)

OTHER PUBLICATIONS

Extended European Search Report dated Jun. 3, 2019, issued in EP Application No. 16818706.0, filed Jun. 29, 2016, 8 pages.
(Continued)

*Primary Examiner* — Sean C. Barron
(74) *Attorney, Agent, or Firm* — Christensen O'Connor Johnson Kindness PLLC (57) ABSTRACT

The present disclosure provides populations of cells comprising partially mature and optimally activated dendritic cells that can be used for administration to individuals having a cancer and/or tumor. Partially matured dendritic cells, those contacted with a dendritic cell maturation agent for about 10 to about 19 hours, upon administration efficiently take up and process tumor antigens in the area of the tumor site, complete maturation, and can subsequently migrate to the lymph nodes of a treated individual. Once in a lymph node the now fully mature antigen presenting dendritic cells secrete the appropriate cytokines (e.g., TNFa,
(Continued)

IL-6, IL-8, and/or IL-12) and contact T cells inducing a substantial and optimal clinical and/or anti-tumor immune response.

11 Claims, 1 Drawing Sheet

(51) Int. Cl.
*A61K 39/00* (2006.01)
*A61P 35/00* (2006.01)

(52) U.S. Cl.
CPC ...... *A61P 35/00* (2018.01); *A61K 2039/5154* (2013.01); *C12N 2501/22* (2013.01); *C12N 2506/11* (2013.01)

(56) References Cited

U.S. PATENT DOCUMENTS

| 2010/0278873 A1 | 4/2010 | Avigan et al. |
| 2010/0215624 A1 | 8/2010 | Kang et al. |
| 2012/0251561 A1 | 10/2012 | Bosch |

FOREIGN PATENT DOCUMENTS

| WO | 00/47719 A2 | 8/2000 |
| WO | 2004/053072 A2 | 6/2004 |
| WO | 2004/076651 A2 | 9/2004 |
| WO | 2009/074341 A1 | 6/2009 |
| WO | 2014/149871 A1 | 9/2014 |

OTHER PUBLICATIONS

Lutz, M.B., et al., "Immature Dendritic Cells Generated With Low Doses of GM-CSF in the Absence of IL-4 are Maturation Resistant and Prolong Allograft Survival in Vivo," European Journal of Immunology 30(7):1813-1822, Jul. 2000.

Sallusto, F. and A. Lanzavecchia, "Efficient Presentation of Soluble Antigen by Cultured Human Dendritic Cells is Maintained by Granulocyte/Macrophage Colony-Stimulating Factor Plus Interleukin 4 and Downregulated by Tumor Necrosis Factor Alpha," The Journal of Experimental Medicine 179(4):1109-1118, Apr. 1994.

International Preliminary Report on Patentability dated Jan. 2, 2018, issued in International Application No. PCT/US2016/040134, filed Jun. 29, 2016, 11 pages.

Search Report dated Oct. 8, 2018, issued in Polish Application No. P-424035, filed Jun. 29, 2016, 2 pages.

International Search Report and Written Opinion dated Oct. 4, 2016, issued in International Application No. PCT/US2016/040134, filed Jun. 29, 2016, 13 pages.

Search Report and Written Opinion dated Apr. 23, 2019, issued in Singapore Application No. 11201710883X, filed Jun. 29, 2016, 9 pages.

Office Action dated Feb. 10, 2021, issued in JP Application No. 2017-567686, filed Jun. 29, 2016, 8 pages.

\* cited by examiner

OPTIMALLY ACTIVATED DENDRITIC CELLS THAT INDUCE AN IMPROVED OR INCREASED ANTI-TUMOR IMMUNE RESPONSE

CROSS-REFERENCES TO RELATED APPLICATIONS

This application is a National Stage of International Application No. PCT/US2016/040134, filed Jun. 29, 2016, which claims the benefit of U.S. Provisional Application No. 62/187,086, filed Jun. 30, 2015, the disclosures of which are hereby incorporated by reference in their entirety.

BACKGROUND

Antigen presenting cells (APCs) are important in eliciting an effective immune response. They not only present antigens to T cells with antigen-specific T cell receptors, but also provide the signals necessary for T cell activation. The ability of APCs to both present antigens and deliver signals for T cell activation is commonly referred to as an accessory cell function. Although monocytes and B cells have been shown to be competent APCs, their antigen presenting capacities in vitro appear to be limited to the re-activation of previously sensitized T cells. Hence, monocytes and B cells are not capable of directly activating functionally naive or unprimed T cell populations. They are also not capable of delivering signals that can polarize an induced immune response, or an immune response as it is induced.

Dendritic cells (DCs) are the professional antigen presenting cells of the immune system that are believed to be capable of activating both naive and memory T cells. Dendritic cells are increasingly prepared ex vivo for use in immunotherapy, particularly the immunotherapy of cancer. The preparation of dendritic cells with optimal immunostimulatory properties requires an understanding and exploitation of the biology of these cells for ex vivo culture. Various protocols for the culture of these cells have been described, with various advantages ascribed to each protocol.

Activation of dendritic cells initiates the process that converts immature DCs, which are phenotypically similar to skin Langerhans cells, to mature, antigen presenting cells that can migrate to the lymph nodes. This process results in the gradual and progressive loss of the powerful antigen uptake capacity that characterizes the immature dendritic cell, and in the up-regulation of expression of co-stimulatory cell surface molecules and various cytokines. Various stimuli can initiate the maturation of DCs. This process is complex and at least in vitro full maturation of monocytic dendritic cells, depending on the dendritic cell maturation agent used, can take up to 48 hours to complete. One other consequence of maturation is a change in the in vivo migratory properties of the cells. For example, the induction of immature dendritic cell maturation induces several chemokine receptors, including CCR7, which direct the cells to the T cell regions of draining lymph nodes, where the mature DCs activate T cells against the antigens presented on the DC surface in the context of class I and class II MHC molecules. The terms "activation" and "maturation", and "activated" and "mature" describe the process of inducing and completing the transition from an immature DC (partially characterized by the ability to take up antigen) to a mature DC (partially characterized by the ability to effectively stimulate de novo T cell responses). The terms typically are used interchangeably in the art.

Known maturation protocols are based on the in vivo environment that DCs are believed to encounter during or after exposure to antigens. An early example of this approach is the use of monocyte conditioned media (MCM) as a cell culture medium. MCM is generated in vitro by culturing monocytes and used as a source of maturation factors. (See for example, US 2002/0160430, incorporated herein by reference.) The major components in MCM responsible for maturation are reported to be the (pro) inflammatory cytokines Interleukin 1 beta (IL-1β), Interleukin 6 (IL-6) and tumor necrosis factor alpha (TNFα).

Maturation of DCs therefore can be triggered or initiated by a multitude of different factors that act via a host of signal transduction pathways. Consequently, there is no single maturation pathway or outcome, but there exists in fact a universe of mature DC stages, each with their own distinct functional characteristics. Conceptually this makes sense because the various threats to the body that the immune system must respond to are manifold, requiring different attack strategies. As an example, while bacterial infection is best cleared by activated macrophages supplemented with specific antibodies, a viral infection is best attacked through cytotoxic T cells that effectively kill virus-infected cells. The killing of cancer cells typically involves a combination of cytotoxic T cells, natural killer cells and antibodies.

In vitro maturation of DCs can therefore be designed to induce the immune system to favor one type of immune response over another, i.e., to polarize the immune response. Directional maturation of DCs describes the notion that the outcome of the maturation process dictates the type of ensuing immune response that results from treatment with the matured DCs. In its simplest form, directional maturation results in a DC population that produces cytokines that direct a T cell response polarized to either a Th1-type or Th2-type immune response. DCs express up to nine different Toll-like receptors (TLR1 through TLR9), each of which can be used to trigger maturation. Not surprisingly, interaction of bacterial products with TLR2 and TLR4 results in directional maturation of DCs resulting in a polarized response most appropriate to dealing with bacterial infections. Conversely, maturation triggered through TLR7 or TLR9 appears to result more in an anti-viral type response. As an additional example, addition of interferon gamma (IFN-γ) to most maturation protocols results in the production of interleukin 12 by the mature DCs, which dictates a Th1-type immune response. Conversely, inclusion of prostaglandin $E_2$ has the opposite effect.

Fully mature dendritic cells differ qualitatively and quantitatively from immature DCs. Once fully mature, DCs express higher levels of MEW class I and class II antigens, and higher levels of T cell co-stimulatory molecules, such as CD80 and CD86. These changes increase the capacity of the dendritic cells to activate T cells because they increase antigen density on the cell surface, as well as the magnitude of the T cell activation signal through the counterparts of the co-stimulatory molecules on the T cells, e.g., CD28 and the like. In addition, mature DCs produce large amounts of cytokines, which stimulate and polarize the T cell response. These cytokines include interleukin 12 associated with a Th1-type immune response and interleukin-10 and interleukin-4 associated with a Th2-type immune response.

Generally methods for ex vivo DC generation comprise obtaining a cell population enriched for DC precursor cells from a subject and then differentiating the DC precursor cells in vitro into fully mature DCs prior to introduction back into the subject. Typically during this process the maturing DCs are contacted with antigen for uptake and processing as the DCs become mature. Some believe that the DCs must be terminally differentiated, or they will de-differentiate back into monocytes/macrophages and lose much of their immune-potentiating ability. Ex vivo maturation of DCs generated from monocytes has been successfully accomplished with methods and agents well known in the art.

Dendritic cells (DCs) are recognized as the vehicle of choice for active immunotherapy of cancer. Animal experiments have demonstrated the potential of DC based immunotherapy in both protecting mice from tumor formation and eliminating established tumors. These successes have been at least partially duplicated in humans in small clinical trials. The transition from small safety- or proof-of-concept trials to larger trials in which activity or efficacy can be demonstrated has been hindered by the laborious and cumbersome nature of DC preparation as described above. As a consequence, few companies have been interested in developing DC-based cancer vaccines despite the large potential therapeutic value of such products.

Intratumoral (IT) injection of DCs is a special form of DC-based immunotherapy. Upon injection, the DCs take up antigen in vivo from, for example, apoptotic or dying tumor cells, and present the antigen(s) to T cells after migration to the lymph nodes. Indeed, it was found that the efficacy of such treatments in animal models correlates with the degree of apoptosis in the tumor (Candido et al., *Cancer Res.* 61:228-236, 2001), which suggests that this approach is fully compatible with treating tumors with chemotherapeutic agents or radiation prior to the injection of DCs. In addition, several groups have demonstrated that such combination therapy is particularly effective against established tumors (Nikitina et al., *Int. J. Cancer* 94:825-833,2001; Tanaka et al., *Int. J. Cancer* 101:265-269, 2002; Tong et al., *Cancer Res.* 61:7530-7535, 2001).

Since the in vivo tumor cells are the source of antigen, IT injection foregoes the need for both the selection and manufacturing of tumor antigens as they are currently used in most in vitro DC based therapy approaches. Selection of a tumor antigen is often driven by the need for companies to have a proprietary position and the few tumor antigens identified to date have yet to be proven to provide significant clinical benefit. In addition, the use of such tumor antigens often results in a monovalent vaccine, which can lose its effectiveness if the tumor cells down regulate the expression of the antigen used in immunization. Of course, the need to manufacture the tumor antigen under conditions required under Good Manufacturing Practices (GMP) adds additional cost to classical DC-based immunization methods.

IT injection of DCs subjects the dendritic cells to an immunosuppressive tumor environment. Tumors are known to produce cytokines that inactivate the DCs or that have the ability to skew T cell response toward a less effective Th2-type immune response. Several groups have used genetic modification of DCs to attempt to overcome these suppressive effects, especially through the production of the cytokine Interleukin 12 (IL-12; Nishioka et al., *Cancer Res.* 59:4035-4041, 1999; Melero et al., *Gene Therapy* 6: 1779-1784, 1999) or expression of CD40 ligand (Kikuchi et al., *Blood* 96:91-99,2000). The encouraging results described by these groups further demonstrate the viability of IT injection of DCs as a therapeutic approach.

Triozzi et al. (*Cancer* 89:2647-2654, 2000) describe IT injection of DCs in patients with metastatic melanoma or breast cancer. They obtained tumor regression in 4 patients with melanoma and in two patients with breast carcinoma. Biopsies of the regressing lesions demonstrated infiltrating T cells, suggesting that the DC had indeed activated an immune response against the tumor cells. Overall these data demonstrated that IT injection of DCs was feasible in humans, and could provide significant clinical benefit. However, significant down regulation of MHC class II antigens and of the B7-2 co-stimulatory molecule on injected DCs has been observed. Down regulation of these critical molecules would be expected to reduce the immunostimulatory potential of the DCs.

One method to overcome this down regulation has been disclosed in WO 2004/053072 (incorporated herein by reference) where it was found that down regulation can be avoided through partial maturation of the DCs prior to administration. In this method dendritic cell precursors (bone marrow cells following red cell lysis or monocytic dendritic cell precursors) were induced in vitro to differentiate into immature dendritic cells and the immature dendritic cells were induced to begin maturation by culturing the cells with a dendritic cell maturation agent, such as BCG and IFNγ, lipopolysaccharide (LPS), tumor necrosis factor α (TNFα), an imidazoquinoline compound, a synthetic double stranded polyribonucleotide, a agonist of a Toll-like receptor (TLR), a sequence of nucleic acids containing unmethylated CpG motifs known to induce the maturation of DC, or any combination thereof. The immature dendritic cells were allowed to continue maturation for a time period less than what had previously been determined for the immature dendritic cells to fully mature. If the dendritic cells were allowed to fully mature in vitro the cells would be unable to uptake and process antigen subsequent to administration to the patient. The inventors disclosed that the dendritic cells should be allowed to mature for 1 to about 10 hours for optimal activation prior to isolation of the partially mature dendritic cells and formulation for administration to a patient.

Unexpectedly it has been determined that immature dendritic cells contacted with a dendritic cell maturation agent, (for example, BCG and IFNγ) for about 10 to about 19 hours are optimally activated for uptake and processing of antigen in vivo and the subsequent induction of an anti-tumor response in a subject.

SUMMARY

The present disclosure provides a method for producing isolated activated human dendritic cells, comprising: i) isolating a cell population comprising human PBMCs from peripheral blood; ii) enriching the cell population comprising human PBMCs for human monocytic dendritic cell precursors; iii) culturing the cell population enriched for human monocytic dendritic cell precursors with a tissue culture medium supplemented with an effective amount of a dendritic cell differentiation agent for a time period sufficient to differentiate the human monocytic dendritic cell precursors into immature human dendritic cells; iv) culturing the cell population enriched for immature human dendritic cells with an effective amount of a dendritic cell maturation agent to activate the immature human dendritic cells for about 10 to about 19 hours; and v) isolating and washing the activated human dendritic cells.

In additional embodiment a method for producing isolated activated human dendritic cells is provided wherein the method comprises the steps of: i) isolating a cell population comprising human monocytic dendritic cell precursors; ii) culturing the cell population enriched for human monocytic dendritic cell precursors with a tissue culture medium supplemented with an effective amount of a dendritic cell differentiation agent for a time period sufficient to differentiate the human monocytic dendritic cell precursors into immature human dendritic cells; iii) culturing the cell population enriched for immature human dendritic cells with an effective amount of a dendritic cell maturation agent to activate the immature human dendritic cells for about 10 to about 19 hours; and iv) isolating and washing the activated human dendritic cells.

The methods can use monocytic dendritic cell precursors that are obtained from skin, spleen, bone marrow, thymus, lymph nodes, umbilical cord blood, or peripheral blood. In addition, the monocytic dendritic cell precursors are obtained from the individual subject to be treated or from a healthy individual subject HLA-matched to the individual subject to be treated.

In the methods above the dendritic cell differentiation agent can be GM-CSF alone without other cytokines or GM-CSF in combination with Interleukin 4 (IL-4). Interleukin 7 (IL-7), Interleukin-13 (IL-13) or Interleukin 15 (IL-15), and the like. In a typical embodiment where GM-CSF is used alone non-activated monocytic dendritic cell precursors are used and the tissue culture medium is also supplemented with at least 1% human or animal protein to prevent adhesion of the non-activated monocytic dendritic cell precursors to the tissue culture substrate. The human or animal protein can be an albumin, serum, plasma, gelatin, a poly-amino acid, and the like.

In the methods the dendritic cell maturation agent can be inactivated Bacillus Calmette-Guerin (BCG), interferon γ (IFNγ), lipopolysaccharide (LPS), tumor necrosis factor α (TNFα), an imidazoquinoline compound, a synthetic double stranded polyribonucleotide, for example, poly[I]:poly[C (12)U], a agonist of a Toll-like receptor (TLR), a sequence of nucleic acids containing unmethylated CpG motifs known to induce the maturation of dendritic cells, or any combination thereof. The inactivated BCG can comprise whole BCG, cell wall constituents of BCG, BCG-derived lipoarabidomannans, or BCG components and the inactivated BCG can be heat-inactivated, formalin-treated, heat-inactivated and formalin treated, and the like.

When used in one of the above methods the effective amount of BCG is about $10^5$ to about $10^7$ cfu per milliliter of tissue culture media and the effective amount of IFNγ is about 100 to about 1,000 Units per milliliter of tissue culture media. When the above method uses an imidazoquinoline compound, the compound can be an imidazoquinoline-4-amine compound, for example, 4-amino-2-ethoxymethyl-α, α-dimethyl-1H-imidazol[4,5-c]quinolin-1-5 ethanol or 1-(2-methylpropyl)-1H-imidazo[4,5-c]quinolin-4-amine, or a derivative thereof.

A composition comprising the partially mature and optimally activated dendritic cells can be administered directly into the tumor; into a tumor bed subsequent to surgical removal or resection of the tumor; into a tissue area surrounding the tumor; into a lymph node directly draining a tumor area; directly to a circulatory vessel or duct that delivers blood or lymph to the tumor or a tumor afflicted organ; or into the circulatory system such that the cells are delivered to the tumor or tumor afflicted organ.

The partially matured and optimally active dendritic cells produced by any one of the above methods can be administered as an adjuvant to radiation therapy, chemotherapy, or a combination thereof. For example, the partially matured optimally activated dendritic cells can be administered prior to, simultaneous with, or subsequent to radiation therapy, chemotherapy, or a combination thereof.

In another embodiment a method is provided for producing an anti-tumor immune response and/or clinical response comprising administrating a composition comprising a cell population enriched for human dendritic cells that have been partially matured and activated in vitro with a human dendritic cell maturation agent for about 10 to about 19 hours and a pharmaceutically acceptable carrier; wherein the composition is administered into a tumor, a tumor bed or a tissue area surrounding a tumor in an individual in need of such treatment.

In still another embodiment, a composition is provided comprising partially mature and optimally activated human dendritic cells induced to mature by culturing with a human dendritic cell maturation agent for about 10 to about 19 hours, wherein the partially mature and optimally activated dendritic cells produce cytokines associated with an inflammatory response. For example, the cytokines can include tumor necrosis factor a (TNFα), interleukin 6 (IL-6), and/or interleukin 8 (IL-8).

DESCRIPTION OF THE DRAWINGS

The foregoing aspects and many of the attendant advantages of the methods and compositions described herein will become more readily appreciated as the same become better understood by reference to the following detailed description, when taken in conjunction with the accompanying drawing, wherein.

DETAILED DESCRIPTION

Dendritic cells are a diverse population of antigen presenting cells found in a variety of lymphoid and non-lymphoid tissues. (See Liu, *Cell* 106:259-262 (2001); Steinman, *Ann. Rev. Immunol.* 9:271-296 (1991)). Dendritic cells include lymphoid dendritic cells of the spleen, Langerhans cells of the epidermis, and veiled cells in the blood circulation. Collectively, dendritic cells are classified as a group based on their morphology, high levels of surface MHC-class II expression, and absence of certain other surface markers expressed on T cells, B cells, monocytes, and natural killer cells. In particular, monocyte-derived dendritic cells (also referred to as monocytic dendritic cells) usually express CD11c, CD80, CD86, and are HLA-DR$^+$, but are CD14$^-$.

In contrast, monocytic dendritic cell precursors (typically monocytes) are usually CD14$^+$. Monocytic dendritic cell precursors can be obtained from any tissue where they reside, particularly lymphoid tissues such as the spleen, bone marrow, lymph nodes and thymus. Monocytic dendritic cell precursors also can be isolated from the circulatory system.

Peripheral blood is a readily accessible source of monocytic dendritic cell precursors. Umbilical cord blood is another source of monocytic dendritic cell precursors. Monocytic dendritic cell precursors can be isolated from a variety of organisms in which an immune response can be elicited. Such organisms include animals, for example, including humans, and non-human animals, such as, primates, mammals (including dogs, cats, mice, and rats), birds (including chickens), as well as transgenic species thereof.

In certain embodiments, the monocytic dendritic cell precursors and/or immature dendritic cells can be isolated from a healthy subject or from a subject in need of immunostimulation, such as, for example, a cancer patient or other subject for whom cellular immunostimulation can be beneficial or desired (i.e., a subject having a bacterial or viral infection, or a hyperplastic condition, and the like). Dendritic cell precursors and/or immature dendritic cells also can be obtained from an HLA-matched healthy individual for partial activation and administration to an HLA-matched subject in need of immunostimulation.

Dendritic Cell Precursors and Immature Dendritic Cells

Methods for isolating cell populations enriched for dendritic cell precursors, such as non-activated dendritic cell precursors, and immature dendritic cells from various sources, including blood and bone marrow, are known in the art. For example, dendritic cell precursors and immature dendritic cells can be isolated by collecting heparinized blood, by apheresis or leukapheresis, by preparation of buffy coats, rosetting, centrifugation, density gradient centrifugation (e.g., using Ficoll® (such as FICOLL-PAQUE®), PERCOLL® (colloidal silica particles (15-30 nm diameter) coated with non-dialyzable polyvinylpyrrolidone (PVP)), sucrose, and the like), differential lysis of cells, filtration, and the like. In certain embodiments, a leukocyte population can be prepared, such as, for example, by collecting blood from a subject, de-fibrinating to remove the platelets and lysing the red blood cells. Dendritic cell precursors and immature dendritic cells can optionally be enriched for monocytic dendritic cell precursors by, for example, centrifugation through a PERCOLL®gradient, antibody panning, and the like. The term "enriched" as used herein means that the monocytic dendritic cell precursors, immature dendritic cells, or partially mature dendritic cells in the cell population comprise at least 25% of the total number of cells in the population, at least 30%, at least 50%, at least 60%, at least 70%, at least 80% or at least even 90% of the total number of cells in the cell population. Typically, the enriched cells will comprise at least about 50% of the total number of cells in the population. In certain embodiments the enriched cells will comprise at least about 90% and up to about 100% of the total number of cells in the cell population.

Dendritic cell precursors and immature dendritic cells optionally can be prepared in a closed, aseptic system. As used herein, the terms "closed, aseptic system" or "closed system" refer to a system in which exposure to non-sterile, ambient, or circulating air or other non-sterile conditions is minimized or eliminated. Closed systems for isolating dendritic cell precursors and immature dendritic cells generally exclude density gradient centrifugation in open top tubes, open air transfer of cells, culture of cells in tissue culture plates or unsealed flasks, and the like. In a typical embodiment, the closed system allows aseptic transfer of the dendritic cell precursors and immature dendritic cells from an initial collection vessel to a sealable tissue culture vessel without exposure to non-sterile air.

Another reported method for isolating dendritic cell precursors is to use a commercially treated plastic substrate (e.g., beads or magnetic beads) to selectively remove adherent monocytes and other "non-dendritic cell precursors." (See, e.g., U.S. Pat. Nos. 5,994,126 and 5,851,756). The adherent monocytes and non-dendritic cell precursors are discarded while the non-adherent cells are retained for ex vivo culture and maturation. In another method, apheresis cells were cultured in plastic culture bags to which plastic, i.e., polystyrene or styrene, microcarrier beads were added to increase the surface area of the bag.

Cells were cultured for a sufficient period of time for certain cells to adhere to the beads and the non-adherent cells were washed from the bag. (Maffei, et al., Transfusion 40:1419-1420 (2000); WO 02/44338, incorporated herein by reference). In certain other embodiments, monocytic dendritic cell precursors are isolated by loose adherence to a monocyte-binding substrate, as disclosed in WO 03/010292, the disclosure of which is incorporated by reference herein. For example, a population of leukocytes (e.g., isolated by leukapheresis) can be contacted with a monocytic dendritic cell precursor adhering substrate. When the population of leukocytes is contacted with the substrate, the monocytic dendritic cell precursors in the leukocyte population preferentially adhere to the substrate but are not activated to differentiate or mature. Other leukocytes (including other potential dendritic cell precursors) exhibit reduced binding affinity to the substrate, thereby allowing the monocytic dendritic cell precursors to be preferentially enriched on the surface of the substrate.

Suitable substrates include, for example, those having a large surface area to volume ratio. The substrate can be, for example, a particulate or fibrous substrate. Suitable particulate substrates include, for example, glass particles, plastic particles, glass-coated plastic particles, glass-coated polystyrene particles, and other beads suitable for protein absorption. Fibrous substrates suitable for use in the present methods include microcapillary tubes and microvillous membranes, and the like. The particulate or fibrous substrate typically allows the adhered monocytic dendritic cell precursors to be eluted without substantially reducing the viability of the adhered cells. A particulate or fibrous substrate can be substantially non-porous to facilitate elution of monocytic dendritic cell precursors or dendritic cells from the substrate. A "substantially non-porous" substrate is a substrate in which at least a majority of pores present in the substrate are smaller than the cells to minimize entrapping cells in the substrate.

Adherence of the monocytic dendritic cell precursors to the substrate can optionally be enhanced by the addition of a binding media. Suitable binding media include, for example, monocytic dendritic cell precursor culture media (e.g., AIM-V®, RPMI 1640, DMEM, XVIVO 15®, and the like) supplemented, individually or in any combination, with for example, cytokines (e.g., Granulocyte/Macrophage Colony Stimulating Factor (GM-C SF), or GM-C SF in combination with Interleukin 4 (IL-4), Interleukin 15 (IL-15), or Interleukin 13 (IL-13)), blood plasma, serum (e.g., human serum, such as autologous or allogeneic sera), purified proteins, such as serum albumin, divalent cations (e.g., calcium and/or magnesium ions) and other molecules that aid in the specific adherence of monocytic dendritic cell precursors to the substrate, or that prevent adherence of non-monocytic dendritic cell precursors to the substrate. In certain embodiments, the blood plasma or serum can be heated-inactivated. The heat-inactivated plasma can be autologous or heterologous to the leukocytes.

Following adherence of monocytic dendritic cell precursors to the substrate, the non-adhering leukocytes are separated from the monocytic dendritic cell precursor/substrate complexes. Any suitable means can be used to separate the non-adhering cells from the complexes. For example, the mixture of the non-adhering leukocytes and the complexes can be allowed to settle, and the non-adhering leukocytes and media decanted or drained. Alternatively, the mixture can be centrifuged, and the supernatant containing the non-adhering leukocytes decanted or drained from the pelleted complexes. It should be noted that adherence of the monocytic dendritic cell precursors to the substrate does not induce the monocytic dendritic cell precursors to activate and differentiate or mature into immature dendritic cells, mature dendritic cells or macrophage without additional stimulation.

In another method, non-activated monocytic dendritic cell precursors can be isolated from a cell population enriched in leukocytes prepared by the use of a tangential flow filtration device as described in International Patent Application Publication No., WO 2004/000444, filed Jun. 19, 2003, now U.S. Pat. No. 7,695,627, both incorporated herein by reference. A tangential flow filtration device useful for the isolation of a cell population enriched in monocytic dendritic cell precursors can comprise a remover unit having a cross-flow chamber, a filtrate chamber and a filter disposed therebetween. The filter is in fluid communication on one side, the retentate surface, with the cross-flow chamber, and on the other side, the filtrate surface, with the filtrate chamber. The cross-flow chamber has an inlet adapted to introduce a sample of blood constituents comprising leukocytes into the cross-flow chamber and parallel to the retentate surface of the filter. An outlet is also provided in the cross-flow chamber centrally disposed in a portion of the chamber opposite the retentate surface of the filter. The filter suitable for use in the tangential flow filtration device typically has an average pore size ranging from about 1 to about 10 microns. The filter can have an average pore size of about 3 to about 7 microns. A means for providing a predetermined input rate of the sample into the inlet of the cross-flow chamber and a means for controlling a filtration rate of filtrate through the filter and into the filtrate chamber can also be included. The filtration rate controlling means limits the rate of filtration to less than the unopposed filtration rate for the filter. The sample comprising blood constituents can be provided by a source device such as a leukopheresis device or a container comprising a sample collected from a leukopheresis device.

Monocytic dendritic cell precursors and cell populations enriched for the precursors can be cultured ex vivo or in vitro for differentiation, and partial maturation and/or expansion. As used herein, "isolated immature dendritic cells", "dendritic cell precursors", and other "cells", refers to cells that, by human hand, exist apart from their native environment, and are therefore not a product of nature. Isolated cells can exist in purified form, in semipurified form, and/or in a non-native environment. Briefly, in vitro and/or ex vivo dendritic cell differentiation typically involves culturing monocytic dendritic cell precursors, or populations of cells having dendritic cell precursors, in the presence of one or more dendritic cell differentiation agents. Suitable differentiating agents can include, for example, cellular growth factors (e.g., cytokines such as (GM-CSF), or a combination of GM-CSF and Interleukin 4 (1L-4), Interleukin 13 (1L-13), or Interleukin 15 (IL-15), or Interleukin 7 (IL-7)). In certain embodiments, the monocytic dendritic cells precursors are differentiated to form monocyte-derived immature dendritic cells.

The dendritic cell precursors can be cultured and differentiated in suitable in vitro culture conditions. Suitable dendritic cell tissue culture media include, but are not limited to, AIM-V®, RPMI 1640, DMEM, X-VIVO 15®, and the like. The tissue culture media can be supplemented with serum, plasma, amino acids, vitamins, cytokines, such as GM-CSF and/or IL-4, IL-7, IL-13, IL-15, divalent cations, and the like, to promote differentiation of the cells. In certain embodiments, the dendritic cell precursors can be cultured in serum-free media. The culture conditions can optionally exclude any animal-derived products. A typical cytokine combination used with dendritic cell culture medium comprises about 500 units/ml each of GM-CSF and IL-4, IL-7, IL-15 or IL-13. In a typical embodiment where non-activated dendritic cell precursors are used a typical dendritic cell tissue culture medium can be supplemented with GM-CSF without any other cytokine under certain conditions. For example, when GM-CSF is used alone the tissue culture medium is also typically supplemented with a high concentration of human or animal protein to prevent adhesion of the non-activated monocytic dendritic cell precursor to the tissue culture substrate thereby activating maturation of the dendritic cell precursor. Typically the human or animal protein is added at a concentration of greater than 1% and typically is used at a concentration of 10% or less. The human or animal protein can be an albumin, such as human serum albumin, serum, plasma, gelatin, a poly-amino acid, and the like.

Dendritic cell precursors, when differentiated to form immature dendritic cells, are phenotypically similar to skin Langerhans cells. Immature dendritic cells typically are $CD14^-$ and $CD11c^+$, express low levels of CD86 and CD83, and are able to capture soluble antigens via specialized endocytosis.

Dendritic cell maturation agents can include, for example, but are not limited to, BCG, IFNγ, LPS, TNFα, an imidazoquinoline compound, e.g., a imidazoquinoline-4-amine compound, such as 4-amino-2-ethoxymethyl-α,α-dimethyl-1H-imidazol[4,5-c]quinolin-1-ethanol (designated R848) or 1-(2-methylpropyl)-1H-imidazo[4,5-c]quinolin-4-amine, and their derivatives (See for example, WO2000/47719, incorporated herein by reference in its entirety), a synthetic double stranded polyribonucleotide, e.g., poly[I]:poly[C(12) U], and the like, agonists of a Toll-like receptor (TLR), such as TLR-3, TLR-4, TLR-7 and/or TLR-9, a sequence of nucleic acids containing unmethylated CpG motifs known to induce the maturation of DC, and the like, or any combination thereof. Effective amounts of BCG typically range from an equivalent to about $10^5$ to $10^7$ cfu per milliliter of tissue culture media prior to deactivation. Effective amounts of IFNγ typically range from about 100 to about 1000 U per milliliter of tissue culture media.

Bacillus Calmette-Guerin (BCG) is an avirulent strain of *Mycobacterium bovis*. As used herein, BCG refers to whole BCG as well as cell wall constituents, BCG-derived lipoarabidomannans, and other BCG components. BCG is optionally inactivated, such as heat-inactivated BCG, formalin-treated BCG, or by combinations of heat and other inactivation methods, and the like. An effective amount of an imidazoquinoline compound, e.g., a imidazoquinoline-4-amine compound, such as 4-amino-2-ethoxymethyl-α,α-dimethyl-1H-imidazol[4,5-c]quinolin-1-ethanol (designated R848) can be about 1 to about 50 μg/ml of culture medium, more typically 5 to about 10 μg/ml of culture media is used. The imidazoquinoline compound can be used alone or can be combined with, for example BCG and/or IFN), or an additional TLR agonist.

The immature DCs are typically contacted with effective amounts of the dendritic cell maturation agent, such as BCG and IFNγ, for about 10 hour to about 19 hours to induce maturation and to optimally activate, but not fully mature the dendritic cells. Typically at least a 24 hour incubation period is required for complete maturation when BCG and IFNγ are used to mature dendritic cells, and depending on the dendritic cell maturation agent used, a typical incubation period of about 48 to about 72 hours can be required for full maturation. In certain embodiments the time period can be about 10 hours, 11 hours, 12 hours, 13 hours, 14, hours, 15, hours, 16 hours, 17 hours, 18 hours, and up to about 19 hours. In a more typical embodiment the time period for partial maturation and optimal activation of the dendritic cells can be about 15 to about 18 hours, about 15 to about 17 hours, or in a particular embodiment about 16 hours. The immature dendritic cells can be cultured and, partially matured and optimally activated in suitable maturation culture conditions. Suitable tissue culture media include, but are not limited to, AIM-VC), RPMI 1640, DMEM, X-VIVO 15 and the like. The tissue culture media can be supplemented with amino acids; vitamins; cytokines, such as GM-C SF alone (See for example, U.S. Pat. No. 8,389,278, incorporated herein by reference in its entirety, or GM-CSF in combination with IL-4, IL-7, IL-13, or IL-15; divalent cations; and the like, to promote the induction of maturation of the cells. A typical cytokine can be GM-C SF alone with a high concentration of human or animal protein or GM-CSF when used in combination is used at a concentration of about 500 units/ml to about 1000 units/ml of GM-CSF and 100 ng/ml of IL-4, IL-13, or IL-15 is used.

Partial maturation and optimal activation of immature dendritic cells can be monitored by methods known in the art for dendritic cells. Cell surface markers can be detected in assays familiar to the art, such as flow cytometry, immunohistochemistry, and the like. The cells can also be monitored for cytokine production (e.g., by ELISA, another immune assay, or by use of an oligonucleotide array). In DCs cultured and partially matured and optimally activated according to the present description in the presence of a dendritic cell maturation agent, such as for example, but not limited to, BCG and INFγ, an increased level of phosphorylated JAK2 (Janus activated kinase 2) as compared to immature dendritic cells can be measured to indicate the initiation of maturation by methods well known in the art. The induction of the expression of cell surface markers and cytokines, as well as the phosphorylation of signaling molecules, e.g., jak2, is also known as an indicator that dendritic cells are conditioned for the uptake of antigen in vivo and the induction of an immune response once the dendritic cells have been administered to an individual.

The present method comprises subjecting immature dendritic cells to maturation conditions only for a time period necessary to initiate maturation of the immature dendritic cells and to partially mature and optimally activate the dendritic cells. A time period of about 10 to 19 hours incubation with an effective amount of BCG and an effective amount of IFNγ has been found to partially mature and optimally activate the dendritic cells for use as a composition when combined with a pharmaceutically acceptable carrier for administration to a subject. Fully mature DCs lose the ability to take up antigen and display up-regulated expression of co-stimulatory cell surface molecules and various cytokines. Specifically, mature DCs express higher levels of MHC class I and II antigens than immature dendritic cells, and mature dendritic cells are generally identified as being $CD80^+$, $CD83^+$, $CD86^+$, and $CD14^-$. Greater MHC expression leads to an increase in antigen density on the DC surface, while up regulation of co-stimulatory molecules CD80 and CD86 strengthens the T cell activation signal through the counterparts of the co-stimulatory molecules, such as CD28 on the T cells. Partially mature and optimally activated dendritic cells as used in the present disclosure typically comprise those dendritic cells that once exposed to a dendritic cell maturation agent demonstrate an up-regulation in the expression of a co-stimulating molecule on the cell surface as compared with immature dendritic cells. These co-stimulating molecules include, but are not limited to, CD80, CD86 and/or CD54. The cells can or may not express CD83, but the cells do maintain the ability to uptake and process antigen for presentation on the surface of the dendritic cell. In an embodiment of methods of the present application, partially mature dendritic cells are exposed to antigen subsequent to administration. Further, the partially mature and optimally activated dendritic cells can produce one or more of TNF-α, IL-6, IL-8, IL-10 and/or IL-12 which are not typically produced in significant amounts by immature dendritic cells. In one particular embodiment, partially mature and optimally activated dendritic cells contacted for about 16 hours with an effective concentration of both BCG and IFNγ produced 149 ng/1 million dendritic cells in a 24 hour period. Immature dendritic cells contacted with the same concentrations of BCG and IFNγ produced only 50 ng/1 million cells in 24 hours.

Fully mature dendritic cells are not preferred for the present methods and compositions because once they are fully mature the cells no longer efficiently process antigen. Further, immature dendritic cells as used in prior methods which have not been induced to begin maturation are not desired because the immunosuppressive environment typically found within a tumor, or in the tissue surrounding a tumor, include substantial concentrations of cytokines known to prevent the processing of antigen by immature dendritic cells. In the present disclosure, partial maturation and optimal activation of the immature dendritic cells down regulates cytokine receptors on the surface of the cell rendering them less sensitive or responsive to any immunosuppressive effects of cytokines present in the intratumoral space, or surrounding tissue, and provides for cells that can efficiently uptake and process antigens present within the intratumoral space or surrounding tissue. The dendritic cells take up and process substantial amounts of tumor antigen from apoptotic and dying tumor cells found within the intratumoral space or in the surrounding tissue. Once the administered partially matured and optimally activated dendritic cells have effectively matured within the intratumoral space as measured by, for example, the expression of the chemokine receptor CCR7, the dendritic cells migrate to the lymph nodes where the dendritic cells now presenting antigen will contact T cells, particularly naive T cells, to up regulate the immune response to any tumor antigens presented by the dendritic cells.

According to yet another aspect of the description, the various DCs of the disclosure can be preserved, e.g., by cryopreservation as monocytic dendritic cell precursors, immature dendritic cells before maturation, or following partial maturation either in combination with or without a pharmaceutically acceptable carrier. Cryopreservation agents which can be used include but are not limited to dimethyl sulfoxide (DMSO), glycerol, polyvinylpyrrolidone, polyethylene glycol, albumin, dextran, sucrose, ethylene glycol, i-erythritol, D-ribitol, D-mannitol, D-sorbitol, inositol, D-lactose, choline chloride, amino acids, methanol, acetamide, glycerol monoacetate, and inorganic salts. A controlled slow cooling rate can be critical. Different cryoprotective agents and different cell types typically have different optimal cooling rates.

The heat of fusion phase where water turns to ice typically should be minimal. The cooling procedure can be carried out by use of, e.g., a programmable freezing device or a methanol bath procedure. Programmable freezing apparatuses allow determination of optimal cooling rates and facilitate standard reproducible cooling. Programmable controlled-rate freezers such as Cryomed® or Planar® permit tuning of the freezing regimen to the desired cooling rate curve.

After thorough freezing, monocytic precursor cells, immature DCs or partially mature DCs either with or without a pharmaceutically acceptable carrier can be rapidly transferred to a long-term cryogenic storage vessel. In a typical embodiment, samples can be cryogenically stored in liquid nitrogen (−196° C.) or its vapor (−165° C.). Considerations and procedures for the manipulation, cryopreservation, and long term storage of hematopoietic stem cells, particularly from bone marrow or peripheral blood, is largely applicable to the cells of the description. Such a discussion can be found, for example, in the following references, incorporated by reference herein: Taylor et al., *Cryobiology* 27:269-78 (1990); Gorin, *Clinics in Haematology* 15:19-48 (1986); Bone-Marrow Conservation, Culture and Transplantation, Proceedings of a Panel, Moscow, Jul. 2226, 1968, International Atomic Energy Agency, Vienna, pp. 107-186.

Frozen cells are preferably thawed quickly (e.g., in a water bath maintained at 37° C. −41° C.) and chilled immediately upon thawing. It may be desirable to treat the cells in order to prevent cellular clumping upon thawing. To prevent clumping, various procedures can be used, including but not limited to the addition before and/or after freezing of DNase (Spitzer et al., *Cancer* 45: 3075-85 (1980)), low molecular weight dextran and citrate, hydroxyethyl starch (Stiff et al., *Cryobiology* 20: 17-24 (1983)), and the like. The cryoprotective agent, if toxic in humans, should be removed prior to therapeutic use of the thawed partially matured DCs. One way in which to remove the cryoprotective agent is by dilution to an insignificant concentration. Once frozen monocytic dendritic cell precursors, immature dendritic cells, or partially matured DCs have been thawed and recovered, they can then be used in further methods to produce a formulated pharmaceutical product. The formulated partially matured and optimally activated dendritic cells can be administered as described herein with respect to nonfrozen partially matured and optimally activated DCs.

In Vivo Administration of Partially Matured Dendritic Cells

Methods and compositions are provided for administration of partially mature and optimally activated dendritic cells, or a cell population enriched and containing such cells, to a subject having for example, a cancer or a tumor. In certain embodiments, such methods are performed by obtaining dendritic cell precursors or immature dendritic cells, differentiating and partially maturing those cells in the presence of a dendritic cell maturation agent, such as BCG and IFNγ, or any other dendritic cell maturation agent such as those listed above. The partially mature and optimally activated dendritic cells can be formulated with physiologically acceptable carriers, excipients, buffers and/or diluents using methods and compositions well known to the skilled artisan. The partially mature and optimally activated dendritic cells can be administered directly to a subject in need of immunostimulation. Typically, about $10^2$ to about $10^{10}$ cells are suspended in a pharmaceutically acceptable carrier. The cells are injected either into the tumor directly or into a region near to, adjacent to, or in circulatory or lymphatic contact with the tumor or tumor bed to ensure that the cells have access to the cancer or tumor antigen.

For example, but not by limitation, the cells can be administered directly into a tumor, into the tumor bed subsequent to surgical removal or resection of the tumor, into a peritumoral space, into a draining lymph node in direct contact with the tumor, into a blood vessel or lymph duct leading into, or feeding a tumor or organ afflicted by the tumor, e.g., the portal vein or a pulmonary vein or artery, and the like. The administration of the partially mature and optimally activated dendritic cells of the disclosure can be either simultaneous with or subsequent to other treatments for the tumor, such as chemotherapy or radiation therapy.

Further, the partially mature dendritic cells of the disclosure can be co-administered with another agent, which agent acts as an adjuvant to the maturation of the dendritic cell and/or the processing of antigen within the tumor or region near or adjacent to the tumor. In addition, the dendritic cells can also be formulated or compounded into a slow release matrix for implantation into a region in or around the tumor or tumor bed such that cells are slowly released into the tumor, or tumor bed, for contact with the tumor antigens.

A tumor as used in the present disclosure includes solid tumors, such as, for example and not limitation, a sarcoma; a pancreatic tumor; a colorectal tumor; a melanoma; a lung tumor; a breast tumor; an ovarian tumor; a head or neck tumor; a stomach tumor; a prostate tumor; an esophageal tumor; a cervical or vaginal tumor; a brain tumor, such as, for example, a glioblastoma, an astrocytoma, a meningioma, or a medulloblastoma; and the like. Additional solid tumors are also subject to treatment using a composition or method disclosed herein.

Partially mature and optimally activated dendritic cells of the present disclosure can be administered by any means appropriate for the formulation and mode of administration. For example, the cells can be combined with a pharmaceutically acceptable carrier and administered with a syringe, a catheter, a cannula, and the like. As above, the cells can be formulated in a slow release matrix. When administered in this fashion, the formulation can be administered by a means appropriate for the matrix used. Other methods and modes of administration applicable to the present description are well known to the skilled artisan.

Compositions of the present description can be used by themselves in the treatment of an individual. In addition, the compositions can be used in combination with any other method to treat a cancer or a tumor. For example, the methods of the present description can be used in combination with surgical resection of a tumor, chemotherapy (cytotoxic drugs, apoptotic agents, antibodies, and the like), radiation therapy, cryotherapy, brachytherapy, immune therapy (administration of antigen specific mature activated dendritic cells, NK cells, antibodies specific for a cancer cell or a tumor antigen, etc.), and the like. Any and all of these methods can also be used in any combination. Combination treatments can be concurrent or sequential and can be administered in any order as determined by the treating physician.

In another embodiment, the dendritic cells and the recipient subject have the same MHC (HLA) haplotype. Methods of determining the HLA haplotype of a subject are known in the art. In a related embodiment, the partially mature dendritic cells are allogeneic to the recipient subject. The allogeneic cells are typically matched for at least one MHC allele (e.g., sharing at least one but not all MHC alleles). In a less typical embodiment, the dendritic cells and the recipient subject are all allogeneic with respect to each other, but all have at least one MHC allele in common.

An anti-tumor immune response can be measured by any one or more well-known method. For example, an anti-tumor response can be measured by a reduction in the size of a tumor, the induction of tumor cell death or tumor cell necrosis, a reduction in tumor cell proliferation, or by the infiltration of tumor antigen specific T cells (TILs), and the like.

EXAMPLE

The following example is provided merely as illustrative of various aspects of the present description and should not be construed to limit the methods and composition disclosed herein in any way. While a preferred embodiment of the method and/or method has been illustrated and described, it will be appreciated that various changes can be made therein without departing from the spirit and scope of the present description.

In this example immature dendritic cells obtained from a blood sample isolated from a patient with cancer, for example, and not limitation, a tumor that is a solid tissue tumor, such as a sarcoma, a pancreatic tumor, a colorectal tumor, a melanoma, a breast tumor; a lung tumor; and an ovarian tumor, and the like, and immature dendritic cells were cultured in dendritic cell culture media supplemented with GM-CSF alone were induced to mature with inactivated BCG and IFNγ for either 16 or 20 hours prior to being collected and prepared for administration to a patient. It was found that dendritic cells that were partially matured and activated for about 16 hours induced a substantially better clinical response in a patient than the dendritic cells contacted with BCG and IFNγ for about 20 hours.

Patients were subjected to leukopheresis and approximately 10 liters or two blood volumes were processed during the collection. Plasma rates were adjusted to obtain a target hematocrit of approximately 2% for the leukopheresis product. The leukopheresis product was processed for the isolation and purification of monocytes by Tangential Flow Filtration (TFF). The leukopheresis sample, typically a blood bag, was connected to the TFF apparatus and the sample was processed and an enriched monocytic dendritic cell precursor product suspended in culture medium (Phenol red free RPMI-1640) was obtained in a tissue culture bag.

Culture medium supplemented with recombinant human GM-CSF (500 U/ml) was added to the enriched non-activated monocytic dendritic cell precursor product and the cells were placed in an incubator for 5 days of culture. During the 5 days of culture the monocytic dendritic cell precursors converted to immature dendritic cells. After this incubation, heat-killed BCG (1:300 dilution v/v or approximately one (1) BCG particle per live dendritic cell) and Interferon γ (500 to 1,000 U/ml) was added to the immature dendritic cells and the bag was returned to the incubator for an additional 16 to 20 hours for dendritic cell activation. This time period was not sufficient to fully convert the immature dendritic cells to mature dendritic cells.

Following dendritic cell activation, the tissue culture bag was agitated and the contents were drained into 250 ml conical centrifuge tubes. Cold dPBS was added to the bag and any remaining adherent cells were dislodged by manual massaging of the bag. This wash was pooled with the initial cell suspension and the cells were pelleted by centrifugation at 550 x g. The activated dendritic cells were resuspended in a small volume of RPMI-1640, 40% human serum albumin and 10% DMSO. The activated dendritic cells were frozen in aliquots of $3\times10^6$, $8\times10^6$, $17\times10^6$ viable dendritic cells/vial in 1.0 ml/vial. Injection volume per batch was adjusted to, if necessary to deliver a total of 2, 6 or 15 million viable dendritic cells per injection. To prepare an aliquot for injection, a vial was removed from vapor phase liquid nitrogen storage and placed at 20° C. to 25° C. for 5 to 10 minutes. This is sufficient time for complete thawing of the contents. The vial was opened and 1 ml of product was aseptically removed using a syringe. Air was drawn into the syringe to ensure that the needle was empty and then the needle removed. The appropriate injecting needle was then attached to the syringe. The product was pushed back into the injection needle. The tumor was then accessed under real time ultrasound or intermittent guidance (MM or CT, or using a multimodal combination. During product administration a single needle was guided under imaging to be within the periphery of the tumor. Once placement was confirmed, the first injection of the predetermined volume, e.g., 0.2 ml each injection was injected within the tumor if four injections were used.

Forty patients were enrolled in the present study. Most patients entered upon failing other therapies, e.g., with actively progressing cancer. Patients were observed for acute toxicity for two hours following each administration and for clinical and laboratory signs of toxicity and autoimmunity for 30 days after the last immunization. In vitro immunological evaluations were conducted to assess immune responses. Disease progression was measured by physical examination measurements, radiographic means and tumor biopsies to assess tumor response and recurrence. As such, stabilization of tumor growth was considered a positive outcome.

Figure 1:
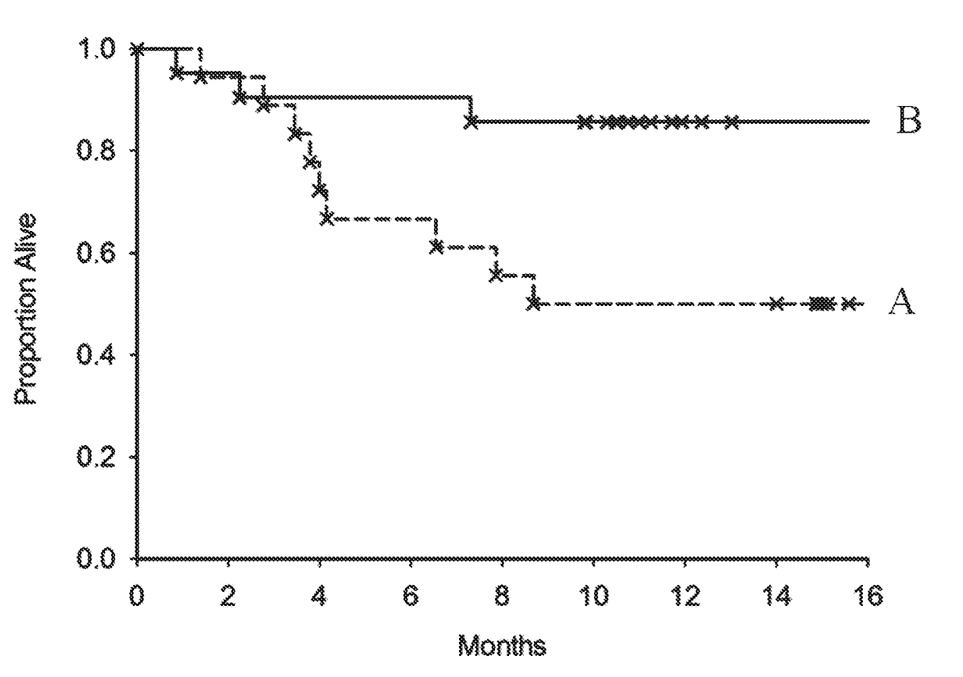
FIG. 1 depicts survival plots for each treatment method. Data points represent the proportion of individuals that remain alive at various time periods measured in months.

The first immunization was given approximately 3 to 4 weeks after leukopheresis. The first three injections were given 1 week apart (i.e., Day 0, Week 1, Week 2), then at weeks 8, 16 and 32, or as long as product was available and for as long as an injectable tumor mass was present at the same site. If there was insufficient tumor mass at the original injection site, a tumor mass at a different location was used. Patients were either provided dendritic cells that had been activated for 16 hours (Method B) or for 20 hours (Method A). A single tumor was injected at each visit and patients were monitored for tumor growth, survival, tumor cell death (necrosis) and infiltration of immune cells. The proportion of individuals alive at each time point is provided in the figure. Tumor growth was measured using standard imaging techniques (either CT or MM).

TABLE 1

Measure of Tumor Growth

| | Overall | Method A | Method B |
|---|---|---|---|
| SD[1] Week 8 | 20 | 4 | 16 |

[1]SD: Stable Disease

Numbers of patients do not add up to 40 because of missing data.

Disease stabilization is a good outcome in this population.

TABLE 2

Measure of Survival

| | Overall | Method A | Method B |
|---|---|---|---|
| Alive | 24 | 5 | 19 |

Stage 4 cancer is a life threatening condition, and survival is an important endpoint.

TABLE 3

Number of Patients demonstrating tumor necrosis

| Overall | Method A | Method B |
|---|---|---|
| 16 patients | 4 patients | 12 patients |

Tumor necrosis was assessed on tumor biopsies, using standard hematoxylin/eosin staining.

Dendritic cells prepared by Method B (16 hour treatment) produce more TNFα than dendritic cells prepared with a less optimal method: average of 149 ng/l million DC/24 hours versus 50 ng/l million DC/24 hours. TNFα is in turn associated with stable disease (SD) at week 8 (see Table 1 above), which is a predictor for better survival (see Table 2 above).

The data demonstrate that a 16 hour treatment (Method B) is optimal for the activation of partially mature DCs for intratumoral injection in cancer immunotherapy.

The embodiments of the invention in which an exclusive property or privilege is claimed are defined as follows:

1. A method for producing isolated partially mature and optimally activated human dendritic cells, comprising:
   i) isolating a cell population comprising human PBMCs from peripheral blood;
   ii) enriching the cell population comprising human PBMCs for human monocytic dendritic cell precursors;
   iii) culturing the cell population enriched for human monocytic dendritic cell precursors with a tissue culture medium supplemented with an effective amount of a dendritic cell differentiation agent for a time period sufficient to differentiate the human monocytic dendritic cell precursors into immature human dendritic cells;
   iv) culturing the cell population enriched for immature human dendritic cells with an effective amount of heat inactivated Bacillus Calmette-Guerin (BCG) and Interferon γ (IFNγ) as a dendritic cell maturation agent to activate the immature human dendritic cells for about 16 hours without contact with an antigen; and
   v) isolating and washing the activated human dendritic cells.

2. A method for producing isolated partially mature and activated human dendritic cells, comprising:
   i) isolating a cell population comprising human monocytic dendritic cell precursors;
   ii) culturing the cell population enriched for human monocytic dendritic cell precursors with a tissue culture medium supplemented with an effective amount of a dendritic cell differentiation agent for a time period sufficient to differentiate the human monocytic dendritic cell precursors into immature human dendritic cells;
   iii) culturing the cell population enriched for immature human dendritic cells with an effective amount of heat inactivated Bacillus Calmette-Guerin (BCG) and Interferon γ (IFNγ) as a dendritic cell maturation agent to activate the immature human dendritic cells for about 16 hours without contact with an antigen; and
   iv) isolating and washing the activated human dendritic cells.

3. The method according to claim 2, wherein the monocytic dendritic cell precursors are obtained from skin, spleen, bone marrow, thymus, lymph nodes, umbilical cord blood, or peripheral blood.

4. The method according to claim 1, wherein the monocytic dendritic cell precursor cells are non-activated monocytic dendritic cell precursors.

5. The method according to claim 1, wherein the monocytic dendritic cell precursors are obtained from an individual subject to be treated.

6. The method according to claim 1, wherein the monocytic dendritic cell precursors are obtained from a healthy individual subject HLA-matched to an individual subject to be treated.

7. The method according to claim 1, wherein the dendritic cell differentiation agent is GM-CSF without any other cytokine, or GM-CSF in combination with IL-4, IL-7, IL-13 or IL-15.

8. The method according to claim 1, wherein the dendritic cell maturation agent is a dilution of inactivated Bacillus Calmette-Guerin (BCG) approximating one BCG particle per dendritic cell, and 500 to 1000 U/mL interferon γ (IFNγ).

9. The method according to claim 8, wherein the inactivated BCG comprises whole BCG, cell wall constituents of BCG, BCG-derived lipoarabidomannans, or BCG components.

10. The method according to claim 9, wherein the inactivated BCG is heat-inactivated BCG, formalin-treated BCG, or heat-inactivated and formalin treated BCG.

11. The method according to claim 8, wherein the effective amount of BCG is about $10^5$ to $10^7$ cfu per milliliter of tissue culture media and the effective amount of IFNγ is about 100 to about 1,000 Units per milliliter of tissue culture media.

* * * * *